(12) United States Patent
Bullock et al.

(10) Patent No.: US 6,462,206 B1
(45) Date of Patent: Oct. 8, 2002

(54) CATALYTIC REDUCTION OF KETONES AND ALDEHYDES USING ORGANOMETALLIC RUTHENIUM COMPLEXES

(75) Inventors: R. Morris Bullock, Wading River, NY (US); Marcel Schlaf, Guelph (CA); Elisabeth M. Hauptman, Wilmington, DE (US)

(73) Assignees: E. I. du Pont de Nemours and Company, Wilmington, DE (US); Brookhaven Science Associates, Upton, NY (US)

( * ) Notice: Subject to any disclaimer, the term of this patent is extended or adjusted under 35 U.S.C. 154(b) by 0 days.

(21) Appl. No.: 09/885,413

(22) Filed: Jun. 20, 2001

(51) Int. Cl.$^7$ .............................................. C07D 305/12
(52) U.S. Cl. ....................... 549/326; 549/273; 560/186; 568/814; 568/821; 568/832; 568/835; 568/881; 585/357; 585/469; 585/733
(58) Field of Search .................. 568/814, 821, 568/835, 832, 881; 585/357, 469, 733; 560/186; 549/273, 326

(56) References Cited

U.S. PATENT DOCUMENTS

| | | | |
|---|---|---|---|
| 4,418,227 A | 11/1983 | Pez et al. | |
| 4,777,302 A | 10/1988 | Haji et al. | |
| 5,614,641 A | 3/1997 | Genet et al. | |
| 6,124,509 A | * 9/2000 | Voges | |
| 6,184,381 B1 | * 2/2001 | Ikariya | |

OTHER PUBLICATIONS

Chinn, M. S., Heinekey, D. M., Payne N. G. and Sofield, C. D., Organometallics, 1989, 8, 1824–1826.
Ohkuma, T., Doucet, H., Pharm, T., Mikami, K., Korenaga, T., Terada, M. and Noyori, R., Journal of American Chemical Society, 1998, 120, 1086–1087.
Osakada, K., Ikariya, T. and Yoshikawa, S., Journal of Organometallic Chemistry, 1982, 231, 79–90.
Fagan, P. J., Mahoney, W. S., Calabrese J. C. and Williams, I. D., American Chemical Society, 1990, 9, 1843–1852.
Chinn, M. S. and Heinekey, D. M. J. Am. Chem. Soc., 1987, 109, 5865–5867.
R.A. Sanchez–Delgado et al, et al., Homogeneous hydrogenation of aldehydes to alcohols with ruthenium complex catalysts, Journal of Organometallic Chemistry, (Apr. 7, 1981) vol. 209, No. 1, pp. 77–83, Elsevier Sequoia, Lausanne, CH.
K. Hata, et al., Vapour phase catalytic hydrogenation of organic compounds using stabilised nickel catalyst, Bulletin of the Chemical Society of Japan, (Sep. 6, 1958) vol. 31, No. 6, pp. 775–776, Tokyo, Japan.

* cited by examiner

Primary Examiner—Michael L. Shippen
(74) Attorney, Agent, or Firm—Inna Y. Belopolsky

(57) ABSTRACT

Ketones and aldehydes are hydrogenated to the corresponding alcohol or alkyl group, using $H_2$ gas as the stoichiometric reductant, and organometallic ruthenium complexes as the catalysts.

17 Claims, No Drawings

CATALYTIC REDUCTION OF KETONES AND ALDEHYDES USING ORGANOMETALLIC RUTHENIUM COMPLEXES

FIELD OF INVENTION

This invention relates to a method of reducing ketones and aldehydes to the corresponding alcohol or alkyl group, using H2 gas as the stoichiometric reductant, and organometallic ruthenium complexes as the catalysts.

BACKGROUND

The homogeneous catalyzed reduction of ketones and aldehydes to various products is an important synthetic reaction in industry. Ruthenium complexes are well known catalysts for the reduction of ketones and aldehydes to various end products. Often phosphorus-containing ligands are used to complex the ruthenium (U.S. Pat. No. 5,614,641, U.S. Pat. No. 4,418,227, and Ohkuma, et al., *J. Amer. Chem. Soc.*, 1998, 120, 1086). Typically, phosphorus-containing ligands are expensive, difficult to make and handle, and sensitive to oxygen.

Chinn, et al, (*Organometallics* 1989, 8, 1824–1826) described the synthesis and spectroscopic properties of the unstable dihydrogen complex $[Cp*Ru(CO)_2(H_2)]^+$ which was found to decompose to $\{[Cp*Ru(CO)_2]_2(\mu\text{-H})\}^+OTf^-$, where Cp* indicates a $\eta^5\text{-}C_5Me_5$ group. The dihydrogen complex is synthesized under mild conditions, has no need for oxygen sensitive ligands (e.g., triaryl phosphines, trialkyl phosphines) or nitrogen-based ligands, and is tolerant to acid and water. However, no mention is made of the catalytic activity of any of these complexes.

SUMMARY OF THE INVENTION

The invention is directed to a process for the reduction of a ketone or aldehyde, comprising contacting a compound of the formula $R^1\text{—}C(=O)\text{—}R^2$ with hydrogen in the presence of a catalytically effective amount of a catalyst precursor having the formula $\{[CpM(CO)_2]_2(\mu\text{-H})\}^+Q^-$, wherein M is selected from the group consisting of Ru and Fe, $R^1$ is selected from the group consisting of hydrogen, substituted and unsubstituted alkyl and aryl groups, $R^2$ is selected from the group consisting of substituted and unsubstituted alkyl and aryl groups; Cp is $\eta^5\text{-}C_5R_5$ wherein R is selected from the group consisting of hydrogen, substituted and unsubstituted $C_1\text{-}C_{18}$ alkyl and aryl groups; and $Q^-$ is a non-coordinating or weakly coordinating non-reactive anion. $R_1$ and $R^2$ may form a ring together.

Preferably, M is Ru, $Q^-$ is $OSO_2CF_3^-$, R is selected from the group consisting of hydrogen and methyl, and the compound of the formula $R^1\text{—}C(=O)\text{—}R^2$ is selected from the group consisting of cyclooctanone, levulinic acid, levulinic acid methyl ester, benzylacetone, 3-heptanone, 4-methoxy-acetoacetate, 3-pentanone and propanal.

Also preferably $R^1$ is selected from the group consisting of hydrogen and substituted and unsubstituted alkyl groups, $R^2$ is selected from the groups consisting of substituted and unsubstituted alkyl groups, and the reduction product is an alcohol.

In the case where $R^1$ and $R^2$ have not formed a ring, the process can further comprise the cyclizing of the alcohol to form the corresponding lactone.

The invention is further directed to a process to reduce a ketone or aldehyde to form a compound of the formula $R^1\text{—}CH_2\text{—}R^2$, comprising contacting a compound of the formula $R^1\text{—}C(=O)\text{—}R^2$ with hydrogen in the presence of a catalytically effective amount of a complex having the formula $\{[CpRu(CO)_2]_2(\mu\text{-H})\}^+Q^-$, wherein $R^1$ is selected from the group consisting of hydrogen, substituted and unsubstituted alkyl and aryl groups; $R^2$ is selected from the group consisting of unsubstituted and substituted aryl groups, Cp is $\eta^5\text{-}C_5R_5$ wherein R is selected from the group consisting of hydrogen, and unsubstituted and substituted $C_1\text{-}C_{18}$ alkyl and aryl groups; and $Q^-$ is a non-coordinating or weakly coordinating non-reactive anion. $R^1$ and $R^2$ may form a ring together.

Preferably $Q^-$ is $OSO_2CF_3^-$ and R is selected from the group consisting of hydrogen and methyl, and the compound of formula $R^1\text{—}C(=O)\text{—}R^2$ is selected from the group consisting of 1-acetonaphthalene and acetophenone.

DETAILED DESCRIPTION OF THE INVENTION

In the present description, "alkyl" means an alkyl group containing up to 18 carbon atoms. Common examples of such alkyl groups include methyl, ethyl, propyl, isopropyl, butyl, s-butyl, isobutyl, pentyl, neopentyl, hexyl, heptyl, isoheptyl, 2-ethylhexyl, cyclohexyl and octyl. The alkyl group may be linear, branched, or cyclic.

By "substituted" is meant the addition of one or more substituent groups to a compound or functional group. Said substituent groups do not cause the compound to be unstable or unsuitable for use in an intended reaction, and are inert under reaction conditions. Substituent groups which are generally useful include nitrile, ether, ester, halo, amino (including primary, secondary and tertiary amino), hydroxy, oxo, vinylidene or substituted vinylidene, carboxyl, silyl or substituted silyl, nitro, sulfinyl, and thioether. Highly basic substituents are generally not suitable in the process of present invention unless previously protonated with acid or protected by a suitable protecting group.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which may be mono-, di-, or trisubstituted with halogen, lower alkyl, lower alkoxy, lower alkylthio, trifluoromethyl, lower acyloxy, aryl, heteroaryl, or hydroxy groups. By "aryl" is also meant heteroaryl groups where heteroaryl is defined as 5-, 6-, or 7-membered aromatic ring systems having at least one heteroatom selected from the group consisting of nitrogen, oxygen and sulfur. Examples of heteroaryl groups are pyridyl, pyrimidinyl, pyrrolyl, pyrazolyl, pyrazinyl, pyridazinyl, oxazolyl, furanyl, quinolinyl, isoquinolinyl, thiazolyl, and thienyl. Said heteroaryl groups may contain substituent groups including halogen, lower alkyl, lower alkoxy, lower alkylthio, trifluoromethyl, lower acyloxy, aryl, heteroaryl, and hydroxy.

The following definitions are used herein:

Ar'=3,5-bis(trifluoromethyl)phenyl
Cp*=$\eta^5\text{-}C_5Me_5$
HOTf=$CF_3SO_3H$
OTf$^-$=$OSO_2CF_3^-$
OTf=$OSO_2CF_3$ The present invention provides a process to prepare an alcohol via the hydrogenation of a ketone or aldehyde by contacting a compound of the formula $R^1\text{—}C(=O)\text{—}R^2$ with hydrogen in the presence of a catalytically effective amount of a catalyst precursor, to form an alcohol, wherein $R^1$ is selected from the group consisting of hydrogen, substituted and unsubstituted alkyl and aryl groups; $R^2$ is selected from the group consisting of substituted and unsubstituted alkyl and aryl groups; and $R^1$ and $R^2$ may form a ring together. The catalyst precursor is of the formula $\{[CpM(CO)_2]_2(\mu\text{-}H)\}^+Q^-$ where $Q^-$ is a non-coordinating or weakly coordinating non-reactive anion, M is selected from the group consisting of Fe and Ru, and Cp is $\eta^5\text{-}C_5R_5$ wherein R is selected from the group consisting of hydrogen and substituted and unsubstituted $C_1$–$C_{18}$ alkyl and aryl groups. Preferably $Q^-$ is $OSO_2CF_3^-$, R is hydrogen or methyl and M is Ru.

Preferred compounds of formula $R^1$—C(=O)—$R^2$ include cyclooctanone, levulinic acid, levuliniic acid methyl ester, benzylacetone, 3-heptanone, 4-methoxyacetoacetate, 3-pentanone, and propanal.

By "alcohol" is meant a compound containing an alcohol functionality. By "ketone" it is meant a compound containing a ketone functionality. By "aldehyde" it is meant a compound containing an aldehyde functionality.

The invention also provides a process to cyclize the alcohol to form a corresponding lactone. This may occur spontaneously under the reaction conditions when the keto group of an ester or carboxylic acid is in the γ, δ or higher position relative to the carbonyl group of the reacting aldehyde or ketone, forming a 5-, 6- or higher membered ring, and eliminating an alcohol in the case of an ester, and water in the case of a carboxylic acid. Two examples of this process are illustrated below. The preferred compound for this embodiment is levulinic acid.

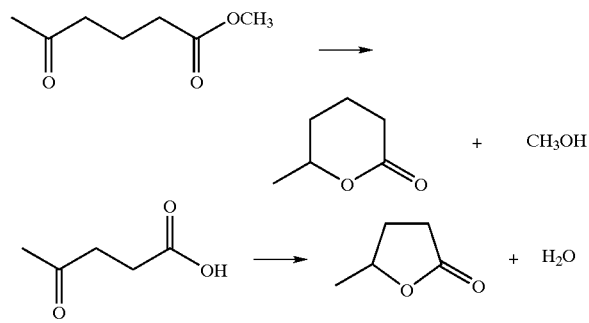

The invention also provides a process to reduce a ketone or aldehyde to form a compound of the formula $R^1$—$CH_2$—$R^2$, comprising contacting a compound of the formula $R^1$—C(=O)—$R^2$ with hydrogen in the presence of a catalytically effective amount of a catalyst precursor, wherein $R^1$ is selected from the group consisting of hydrogen, substituted and unsubstituted alkyl and aryl groups, $R^2$ is selected from the group consisting of unsubstituted and substituted aryl groups, and $R^1$ and $R^2$ may form a ring together. The catalyst precursor is of the formula $\{[CpM(CO)_2]_2(\mu\text{-}H)\}^+Q^-$ where $Q^-$ is a non-coordinating or weakly coordinating non-reactive anion, M is selected from the group consisting of Fe and Ru, and Cp is $\eta^5\text{-}C_5R_5$ wherein R is selected from the group consisting of hydrogen and substituted and unsubstituted $C_1$–$C_{18}$ alkyl and aryl groups. Preferably R is hydrogen or methyl, $Q^-$ is $OSO_2CF_3^-$ and M is Ru. Preferred compounds of the formula $R^1$—C(=O)—$R^2$ include 1-acetonaphthalene and acetophenone.

When either $R^1$ or $R^2$ is a substituted or unsubstituted aryl group, the reaction will follow the path below under most reaction conditions:

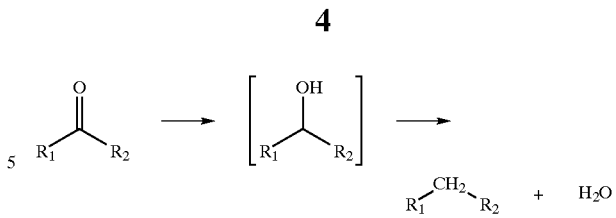

In some instances when an aryl substituent is present, only the alcohol or a mixture of the alcohol and alkyl product can be obtained. When neither of the substituents contains a hydrogen atom on the carbon atom that is alpha to the oxo group only the alcohol is obtained.

The catalytically active species for both processes is believed to be $[CpM(CO)_2]H$ in combination with one or both of the transient complexes $[CpM(CO)_2(\eta^2\text{-}H_2)]^+$ and $[CpM(CO)_2]^+$, all of which are generated under the reaction conditions. Any synthetic route may be used that leads to the same reactive species, such as use of $CpM(CO)_2OQ$, $[CpM(CO)_2]_2$ and $H^+Q^-$, or $CpM(CO)_2H$ and $H^+Q^-$ as catalyst precursors.

The catalyst precursor, $\{[Cp^*Ru(CO)_2]_2(\mu\text{-}H)\}^+OTf^-$, was prepared in the following manner. In a drybox, a flask was charged with $Cp^*Ru(CO)_2H$ (2.05 g, 6.986 mmol, prepared as described in Fagan et al., Organomet., 1990, 9, 1843). The $Cp^*Ru(CO)_2H$ was dissolved in 2 ml of $CH_2Cl_2$. To this flask was added triflic acid (310 μl, 3.5 mmol) slowly, resulting in vigorous gas evolution ($H_2$). Diethyl ether (10 ml). was then added to the flask and a yellow solid precipitated out of solution. The yellow solid was isolated by filtration and rinsed twice with a minimum amount of diethyl ether.

Weakly coordinating anions are known to those skilled in the art. Such anions are often bulky anions, particularly those that may delocalize their negative charge. The coordinating capability of such anions has been discussed in the literature; see, for instance, W. Beck, et al., Chem. Rev., vol. 88, p. 1405–1421 (1988), and S. H. Strauss, Chem. Rev., Vol. 93, p. 927–942 (1993). Weakly coordinating anions suitable for the processes of the present invention include $OSO_2CF_3^-$ (herein abbreviated as $OTf^-$), $SO_4^{2-}$, $HSO_4^-$, $BF_4^-$, $PF_6^-$, $SbF_6^-$, $BPh_4^-$, and $BAr'_4^-$ where Ar'=3,5-bis(trifluoromethyl)phenyl. Most preferred is $OTf^-$.

The processes of the present invention are carried out under an atmosphere of hydrogen gas or any mixture of hydrogen gas with other gases that do not interfere with the desired reaction, such as nitrogen, helium, neon and argon gases. Other in situ sources of hydrogen can also be used. The partial pressure of the hydrogen should be between about 14 to about 1000 psi (0.1 to 7.0 MPa), preferably about 14 to about 800 psi (0.1 to 5.5 MPa). The temperature range is about 40° C. to about 120° C., preferably about 65° C. to about 110° C. The temperature and pressure range can vary depending on the selection of solvent, providing the aldehyde or ketone and solvent remain in the liquid phase.

The processes may be run neat or a suitable solvent may be used. Suitable solvents are non-coordinating, non-basic, inert and able to partially dissolve the catalyst precursor under the reaction conditions. The solvents may be deuterated for ease of analysis. Preferred solvents are dichlorobenzene, sulfolane (tetramethylene sulfone; tetrahydrothiophene-1,1-dioxide) and $CH_2Cl_2$.

EXAMPLES

Reactions of the following examples were carried out in a reactor composed of a glass vial inside a stainless steel pressure vessel, which can be easily assembled by one skilled in the art.

Example 1

HYDROGENATION OF 1-ACETONAPHTHALENE TO 1-ETHYLNAPHTHALENE

A 2 mL reactor was charged with 0.150 mL of a 1.00 M solution of 1-acetonaphthalene and 0.050 mL of a 0.030 M solution of $\{[Cp^*Ru(CO)_2]_2(\mu\text{-}H)\}^+OTf^-$ in dichlorobenzene. The reaction was heated at 90° C. for 12 hours at 820 psi (5.7 MPa) of hydrogen gas. The reaction was cooled, and analyzed using gas chromatography/mass spectroscopy. Analysis indicated 100% conversion of the 1-acetonaphthalene, with a greater than 90% yield of 1-ethylnaphthalene. Note that in this example, the alcohol itself (presumably initially formed from hydrogenation of the C=O double bond) undergoes a hydrogenation reaction to yield in the final product, 1-ethylnaphthalene.

Example 2

HYDROGENATION OF LEVULINIC ACID METHYL ESTER TO γ-VALEROLACTONE

A 2 mL reactor was charged with 0.150 mL of a 1.00 M solution of levulinic acid methyl ester in dichlorobenzene, and 0.050 mL of a 0.030 M solution of $\{[Cp^*Ru(CO)_2]_2(\mu\text{-}H)\}^+OTf^-$ in dichlorobenzene. The reactor was heated to 90° C. for 12 hours at 820 psi (5.7 MPa) of hydrogen gas. The reaction was cooled, and analyzed using gas chromatography/mass spectroscopy. Analysis indicated 100% conversion of the levulinic acid methyl ester, with a greater than 90% yield of γ-valerolactone. Note that in this case, the alcohol itself (presumably initially formed from hydrogenation of the C=O double bond) reacts further to reach the final product, a lactone resulting from a ring-closure reaction.

Example 3

HYDROGENATION OF CYCLOOCTANONE TO CYCLOOCTANOL

A 2 mL reactor was charged with 0.150 mL of a 1.00 M solution of cyclooctanone and 0.050 mL of a 0.030 M solution of $\{[Cp^*Ru(CO)_2]_2(\mu\text{-}H)\}^+OTf^-$ in dichlorobenzene. The reaction was heated at 90° C. for 12 hours at 820 psi (5.7 MPa) of hydrogen gas. The reaction was cooled, and analyzed using gas: chromatography/mass spectroscopy. Analysis indicated 90% conversion of the cyclooctanone with a greater than 80% yield of cyclooctanol.

Example 4

HYDROGENATION OF BENZYLACETONE TO 4-PHENYL-2-BUTANOL

A 2 mL reactor was charged with 0.150 mL of a 1.00 M solution or benzylacetone and 0.050 mL of a 0.030 M solution of $\{[Cp^*Ru(CO)_2]_2(\mu\text{-}H)\}^+OTP^-$ in dichlorobenzene. The reaction was heated at 90° C. for 12 hours at 820 psi (5.7 MPa) of hydrogen gas. The reaction was cooled, and analyzed using gas chromatography/mass spectroscopy. Analysis indicated 100% conversion of the benzylacetone, with a greater than 90% yield of 4-phenyl-2-butanol.

Example 5

HYDROGENATION OF 3-HEPTANONE TO 3-HEPTANOL

A 2 mL reactor was charged with 0.150 mL of a 1.00 M solution of 3-heptanone and 0.050 mL of a 0.030 M solution of $\{[Cp^*Ru(CO)_2]_2(\mu\text{-}H)\}^+OTf^-$ in dichlorobenzene. The reaction was heated at 90° C. for 12 hours at 820 psi (5.7 MPa) of hydrogen gas. The reaction was cooled, and analyzed using gas chromatography/mass spectroscopy. Analysis indicated 100% conversion of the 3-heptanone with a greater than 90% yield of 3-heptanol.

Example 6

HYDROGENATION OF METHYL 4-METHOXYACETOACETATE TO 3-HYDROXY-4-METHOXYBUTYRIC ACID METHYL ESTER.

A 2 mL reactor was charged with 0.150 mL of a 1.00 M solution of 4-methoxyacetoacetate and 0.050 mL of a 0.030 M solution of $\{[Cp^*Ru(CO)_2]_2(\mu\text{-}H)\}^+OTf^-$ in dichlorobenzene. The reaction was heated at 90° C. for 12 hours at 820 psi (5.7 MPa) of hydrogen gas. The reaction was cooled, and analyzed using gas chromatography/mass spectroscopy. Analysis indicated 100% conversion of the 4-methoxyacetoacetate with a greater than 90% yield of 3-hydroxy-4-methoxybutyric acid methyl ester.

Example 7

HYDROGENATION OF 3-PENTANONE TO 3-PENTANOL

A solution of 3-pentanone (0.14 M) and of $\{[Cp^*Ru(CO)_2]_2(\mu\text{-}H)\}^+OTf^-$ (0.028 M) in $CD_2Cl_2$ (0.68 mL) was placed under hydrogen gas (45 psi, 0.31 MPa). The solution was heated for 5 days at 65° C. Analysis by $^1H$ nuclear magnetic resonance (NMR) spectroscopy indicated a greater than 90% yield of 3-pentanol.

Example 8

HYDROGENATION OF NEAT 3-PENTANONE TO 3-PENTANOL

A solution of $\{[Cp^*Ru(CO)_2]_2(\mu\text{-}H)\}^+OTf^-$ (0.0071 M) in 3-pentanone (3.6 mL) was placed under hydrogen (790 psi, 5.4 MPa) and heated for 5 days at 88° C. Analysis by I H nuclear magnetic resonance (NMR) spectroscopy indicated a >90% yield of 3-pentanol and a small amount (<10%) of the ether $[(C_2H_5)_2CH]_2O$, which forms by acid-catalyzed condensation of the alcohol product.

Example 9

HYDROGENATION OF ACETOPHENONE TO ETHYLBENZENE

A solution of acetophenone (0.19 M) and of $\{[Cp^*Ru(CO)_2]_2(\mu\text{-}H)\}^+OTf^-$ (0.028 M) in $CD_2Cl_2$ (0.55 mL) was placed under hydrogen gas (45 psi, 0.31 MPa). The solution was heated for 4 days at 85° C. Analysis by I H nuclear magnetic resonance (NMR) spectroscopy indicated about 91% yield of ethylbenzene and 9% of acetophenone remaining.

Example 10

HYDROGENATION OF PROPANAL TO n-PROPYL ALCOHOL

A solution of propanal (1.0 M) and of $\{[Cp^*Ru(CO)_2]_2(\mu\text{-}H)\}^+OTf^-$ (0.005 M) in sulfolane (50 mL) was placed under hydrogen gas (750 psi, 5.2 MPa). Toluene (0.1 M) was present in the solution as an internal standard for determination of the yield. The solution was heated for 18 hours at 100° C. Analysis by gas chromatography (GC) indicated a 62% yield of n-propanol, with less than 3% propanal remaining.

What is claimed is:

1. A process for the reduction of a ketone or aldehyde, comprising:

contacting a compound of the formula $R^1$—C(=O)—$R^2$ with hydrogen in the presence of a catalytically effective amount of a catalyst precursor having the formula $\{[CpM(CO)_2]_2(\mu\text{-H})\}^+Q^-$;

wherein M is selected from the group consisting of Ru and Fe;

$R^1$ is selected from the group consisting of hydrogen, substituted and unsubstituted alkyl and aryl groups;

$R^2$ is selected from the group consisting of substituted and unsubstituted alkyl and aryl groups, wherein $R^1$ and $R^2$ together can form a ring;

Cp is $\eta^5$-$C_5R_5$ wherein R is selected from the group consisting of hydrogen, substituted and unsubstituted $C_1$–$C_{18}$ alkyl and aryl groups; and $Q^-$ is a non-coordinating or weakly coordinating non-reactive anion.

2. The process according to claim 1 wherein M is Ru.

3. The process according to claim 1 wherein $R^1$ is selected from the group consisting of hydrogen and substituted and unsubstituted alkyl groups, and $R^2$ is selected from the groups consisting of substituted and unsubstituted alkyl groups.

4. The process according to claim 1 wherein $R^1$ and $R^2$ together form a ring.

5. The process according to claim 1 wherein $Q^-$ is $OSO_2CF_3^-$ and R is selected from the group consisting of hydrogen and methyl.

6. The process according to claim 1 wherein the compound of the formula $R^1$—C(=O)—$R^2$ is: selected from the group consisting of cyclooctanone, levulinic acid, levulinic acid methyl ester, benzylacetone, 3-heptanone, 4-methoxyacetoacetate, 3-pentanone, propanal, 1-acetonaphthalene and acetophenone.

7. The process according to claim 1 wherein the process produces an alcohol.

8. The process according to claim 7 further comprising cyclizing the alcohol to form a corresponding lactone.

9. The process according to claim 7 wherein the alcohol is levulinic acid or levulinic acid methyl ester.

10. The process according to claim 1 wherein $R^2$ is selected from the group consisting of unsubstituted and substituted aryl groups.

11. The process according to claim 10 wherein the process forms a ompound having the formula $R^1$—$CH_2$—$R^2$.

12. The process according to claim 11 wherein $R^1$ and $R^2$ together form a ring.

13. The process according to claim 12 wherein $Q^-$ is $OSO_2CF_3^-$ and R is selected from the group consisting of hydrogen and methyl.

14. The process according to claim 13, wherein the compound of formula $R^1$—C(=O)—$R^2$ is selected from the group consisting of 1-acetonaphthalene and acetophenone.

15. The process according to claim 1 wherein the process is carried out at a temperature of about 65° C. to about 110° C.

16. The process according to claim 1 wherein the process is carried out at a pressure of about 0.1 MPa to about 5.5 MPa.

17. The process according to claim 1 wherein the process is carried out in a solvent selected from the group consisting of dichlorobenzene, sulfolane or $CH_2Cl_2$.

* * * * *

UNITED STATES PATENT AND TRADEMARK OFFICE
CERTIFICATE OF CORRECTION

PATENT NO.    : 6,462,206 B1
DATED         : October 8, 2002
INVENTOR(S)   : Elizabeth Hauptman et al.

It is certified that error appears in the above-identified patent and that said Letters Patent is hereby corrected as shown below:

<u>Title page,</u>
Item [75], please insert -- Paul Fagan, Wilmington, DE (US) -- before last inventor.

Signed and Sealed this

Eighth Day of April, 2003

JAMES E. ROGAN
*Director of the United States Patent and Trademark Office*